(12) United States Patent
Cordoba et al.

(10) Patent No.: US 10,780,256 B2
(45) Date of Patent: Sep. 22, 2020

(54) SYSTEM FOR INTEGRATING AN ANTIBACTERIAL-ELEMENT RECEPTACLE INTO AN AUTOINJECTOR CAP

(71) Applicant: Silcor Biomed, LLC, Deerfield Beach, FL (US)

(72) Inventors: Silvestre Cordoba, Deerfield Beach, FL (US); Frank A. Scarfone, Miramar, FL (US)

(73) Assignee: Silcor Biomed, LLC., Deerfield Beach, FL (US)

( * ) Notice: Subject to any disclaimer, the term of this patent is extended or adjusted under 35 U.S.C. 154(b) by 261 days.

(21) Appl. No.: 15/925,648

(22) Filed: Mar. 19, 2018

(65) Prior Publication Data

US 2018/0264243 A1 Sep. 20, 2018

Related U.S. Application Data

(60) Provisional application No. 62/472,875, filed on Mar. 17, 2017.

(51) Int. Cl.

| | |
|---|---|
| *A61M 5/00* | (2006.01) |
| *A61F 13/40* | (2006.01) |
| *A61F 13/38* | (2006.01) |
| *A61M 5/32* | (2006.01) |

(52) U.S. Cl.
CPC ........... *A61M 35/006* (2013.01); *A61F 13/38* (2013.01); *A61M 5/001* (2013.01); *A61M 5/3202* (2013.01); *A61M 5/3204* (2013.01); *A61M 5/002* (2013.01); *A61M 2205/0205* (2013.01)

(58) Field of Classification Search
CPC .. A61M 35/006; A61M 5/001; A61M 5/3202; A61M 5/3204; A61M 39/162; A61M 39/165; A61M 2005/2073; A61M 2005/2013; A61M 2005/208
See application file for complete search history.

(56) References Cited

U.S. PATENT DOCUMENTS

| | | | | |
|---|---|---|---|---|
| 4,799,926 | A * | 1/1989 | Haber | ..................... A61M 5/31 604/1 |
| 5,425,715 | A * | 6/1995 | Dalling | ............... A61M 5/2033 604/135 |
| 2013/0053751 | A1 | 2/2013 | Holtham | |
| 2015/0080809 | A1 * | 3/2015 | Dasbach | ........... A61M 5/31555 604/198 |

* cited by examiner

*Primary Examiner* — Bhisma Mehta
*Assistant Examiner* — James D Ponton

(57) ABSTRACT

A system for integrating an antibacterial-element receptacle into an autoinjector cap facilitates the pre-injection treatment, the post-injection treatment, and prevents the accidental delivery of the injection. The system includes a cap assembly, an autoinjector body, and an antiseptic-soaked dressing. The cap assembly encloses the needle of the autoinjector and prevents the accidental trigger of the injection mechanism. The autoinjector body refers to the body of any conventional autoinjector. The antiseptic-soaked dressing is applied to the patient's skin prior to the delivery of the injection to disinfect and sterilize the injection area. The antiseptic-soaked dressing is housed in the cap assembly, between a receptacle and a removable cover. The removable cover is releasably mounted to the receptacle to allow access to the antiseptic-soaked dressing.

14 Claims, 9 Drawing Sheets

SYSTEM FOR INTEGRATING AN ANTIBACTERIAL-ELEMENT RECEPTACLE INTO AN AUTOINJECTOR CAP

The current application claims a priority to the U.S. Provisional Patent application Ser. No. 62/472,875 filed on Mar. 17, 2017. The current application is filed on Mar. 19, 2018 while Mar. 17, 2018 was on a weekend.

FIELD OF THE INVENTION

The present invention generally relates to a system for attaching an antiseptic element receptacle into an autoinjector cap. More specifically, the antiseptic element receptacle facilitates the pre-treating of the injection area, the administration of the injection, and in some embodiments, the post-injection treatment process.

BACKGROUND OF THE INVENTION

There are many different forms of syringes for administering medication in their liquid or gas forms. Although many of these syringes can only be delivered by trained medical personnel, many are intended to be self-administered by the patient. An autoinjector is a medical device designed to deliver a single dose of a (typically life-saving) drug. By design, most autoinjectors are spring loaded syringes that are easy to operate and can be operated by untrained personnel or by the patients themselves.

Before administering the injection via a syringe or an autoinjector, it is important for the injection site, where the needle is to subcutaneously penetrate the patient's skin, to be disinfected and free of germs that can cause infections and post-injection complications. Typically, the administrator swabs the injection site with a dressing infused with an antiseptic, antibacterial solution. The dressing is typically a cloth swab pre-soaked with the antiseptic or may be used in conjunction with a bottle of an antiseptic and that is poured onto the swab just before the pre-treatment of the injection area. One of the issues with home autoinjector usage is that it is not always convenient to have the swabs or other types of cleansing items available when it is time to administer a drug via injection. The swabs themselves are normally sold in large, bulky quantities that are difficult to carry and transport. In most cases, swabs are stored in medical kits carried by medical personnel. Further, it is also possible for the patient to be out of swabs or the antiseptic, antibacterial solution when the trying to deliver the injection.

Thus, there exists a need for a system to integrate swabs and antiseptic, antibacterial solutions, into a compact, easy-to-carry package that can be mounted to the autoinjector of syringe itself. More specifically, the present invention utilizes an autoinjector cap capable of holding materials for both the pre-injection treatment process and the post-injection treatment process.

SUMMARY OF THE INVENTION

The present invention is a system for integrating an antibacterial element receptacle into an autoinjector cap. The system includes an autoinjector cap assembly coupled to a needle-end of the autoinjector housing. The cap assembly contains an antiseptic-soaked dressing. The cap assembly includes a removable cover and a receptacle for enclosing the antiseptic-soaked dressing. In one possible embodiment, the antiseptic-soaked dressing may be positioned into an opening of the receptacle, allowing the antiseptic-soaked dressing to be utilized while the cap assembly is attached to the autoinjector body. In another possible embodiment of the present invention, the cap assembly contains a storage compartment for storing post-injection treatment materials. Further, in this embodiment, the antiseptic-soaked dressing is mounted into an opening of the removable cover, thereby requiring the administrator to remove the cap assembly from the autoinjector body for the pre-injection treatment process. In yet another embodiment, the cap assembly is locked to the autoinjector body via an expiration timer and a locking mechanism. The expiration timer is programmed to engage the locking mechanism once the expiration date of the autoinjector medicine passes.

DETAILED DESCRIPTION OF THE INVENTION

All illustrations of the drawings are for the purpose of describing selected versions of the present invention and are not intended to limit the scope of the present invention.

The present invention is a system for integrating an antibacterial element receptacle into an autoinjector cap. By mating the antibacterial element to the autoinjector cap, the present invention facilitates the pre-treating of the injection area, the administration of the injection, and in some embodiments, the post-injection treatment process.

Figure 1:
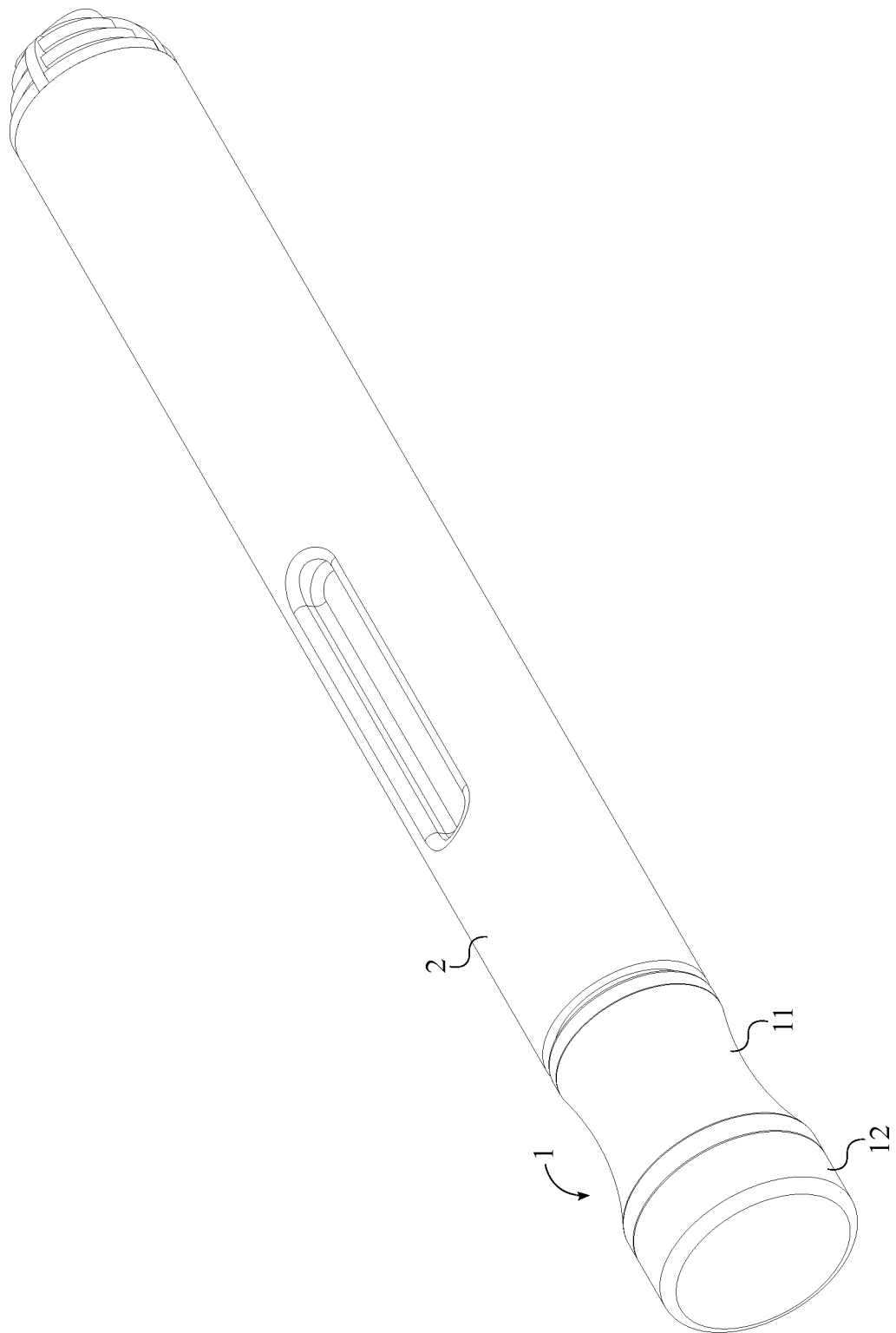
FIG. 1 is a front perspective view of the present invention, wherein the antiseptic-soaked dressing is attached to the receptacle.
Figure 2:
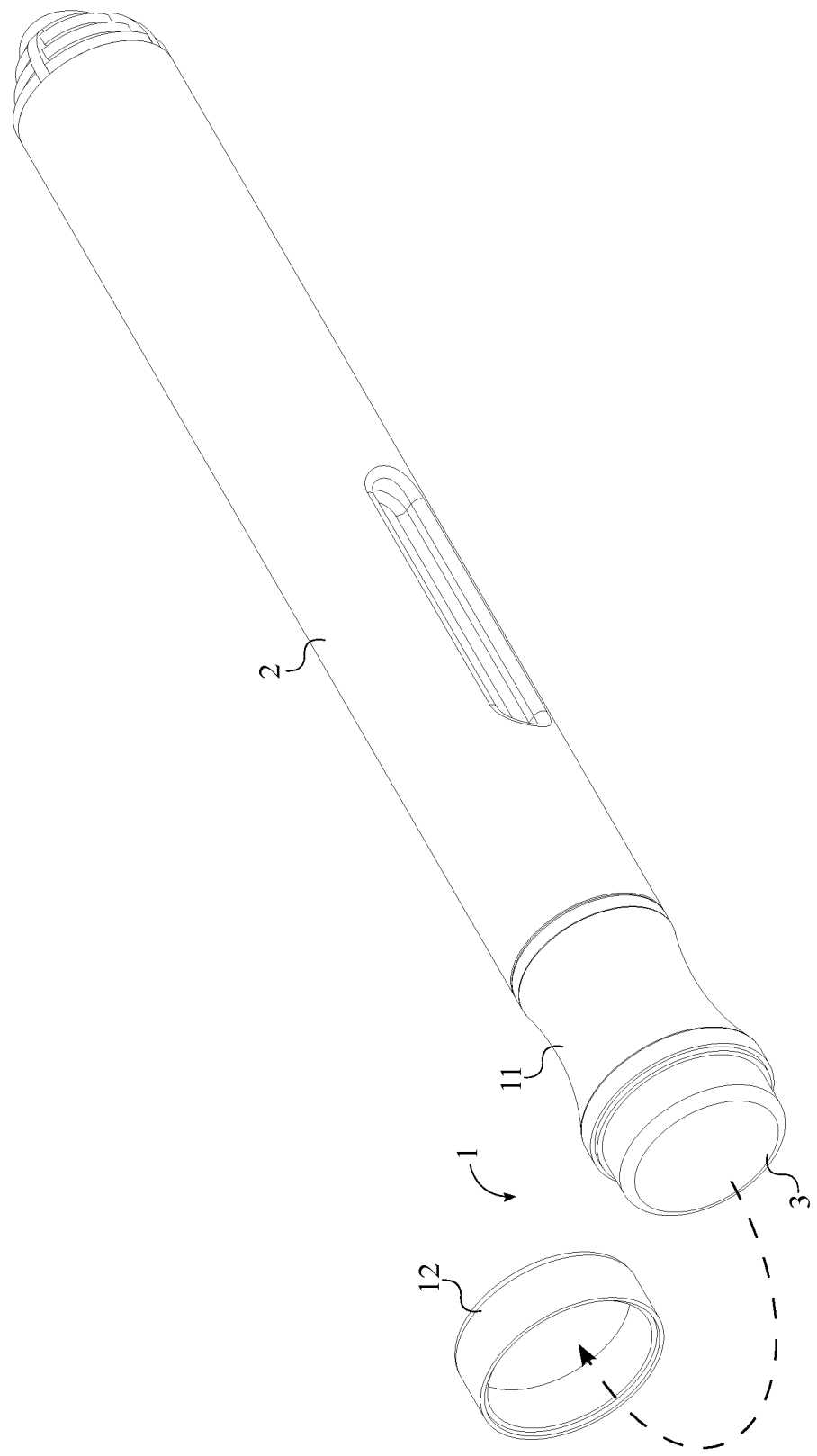
FIG. 2 is a front perspective view illustrating the cap assembly with the removable cover detached from the receptacle.

In reference to FIG. 1 and FIG. 2, the preferred embodiment of the present invention comprises a cap assembly 1, an autoinjector body 2, and an antiseptic-soaked dressing 3. The cap assembly 1 covers the needle of the autoinjector until the injection needs to be administered to a patient. The cap assembly 1 of the present invention, in addition to covering the needle, houses materials that are required for the pre-injection treatment. The cap assembly 1 must be made of materials that can be easily sterilized such as carbon steel, stainless steel, aluminum, Titanium, other metals or alloys, composites, ceramics, polymeric materials such as polycarbonates. Preferably, the cap assembly 1 is designed to be retrofitted onto an existing autoinjector. As such, the autoinjector body 2 refers to the body of any conventional autoinjector known in the public domain. Alternately, the cap assembly 1 may be retrofitted onto a conventional plastic syringe. Finally, the antiseptic-soaked dressing 3 is wiped onto the skin of the patient, where the injection is to be administered.

Figure 3:
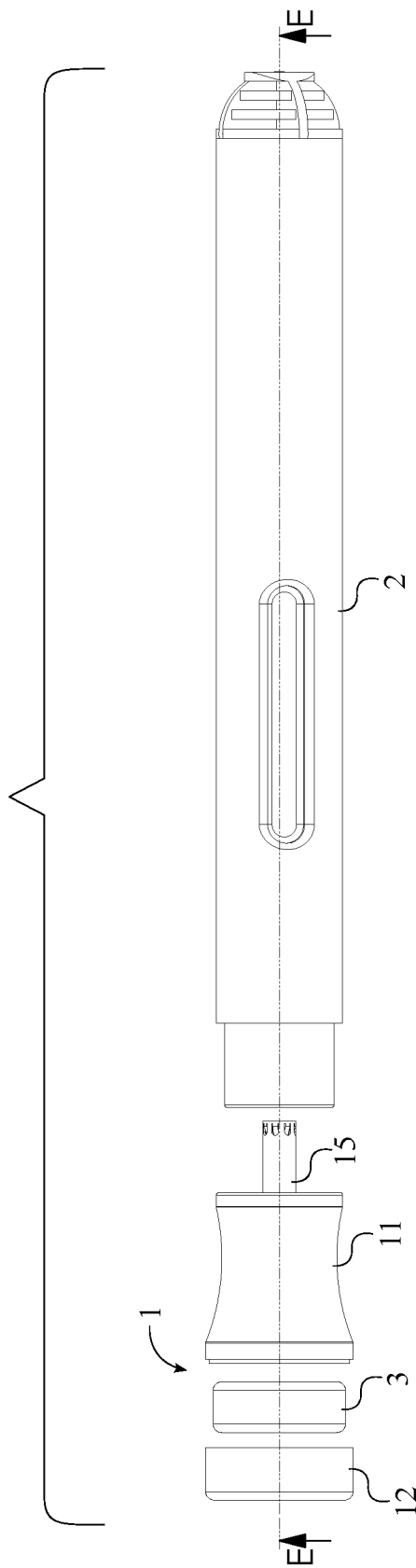
FIG. 3 is a top exploded view of the present invention.
Figure 4:
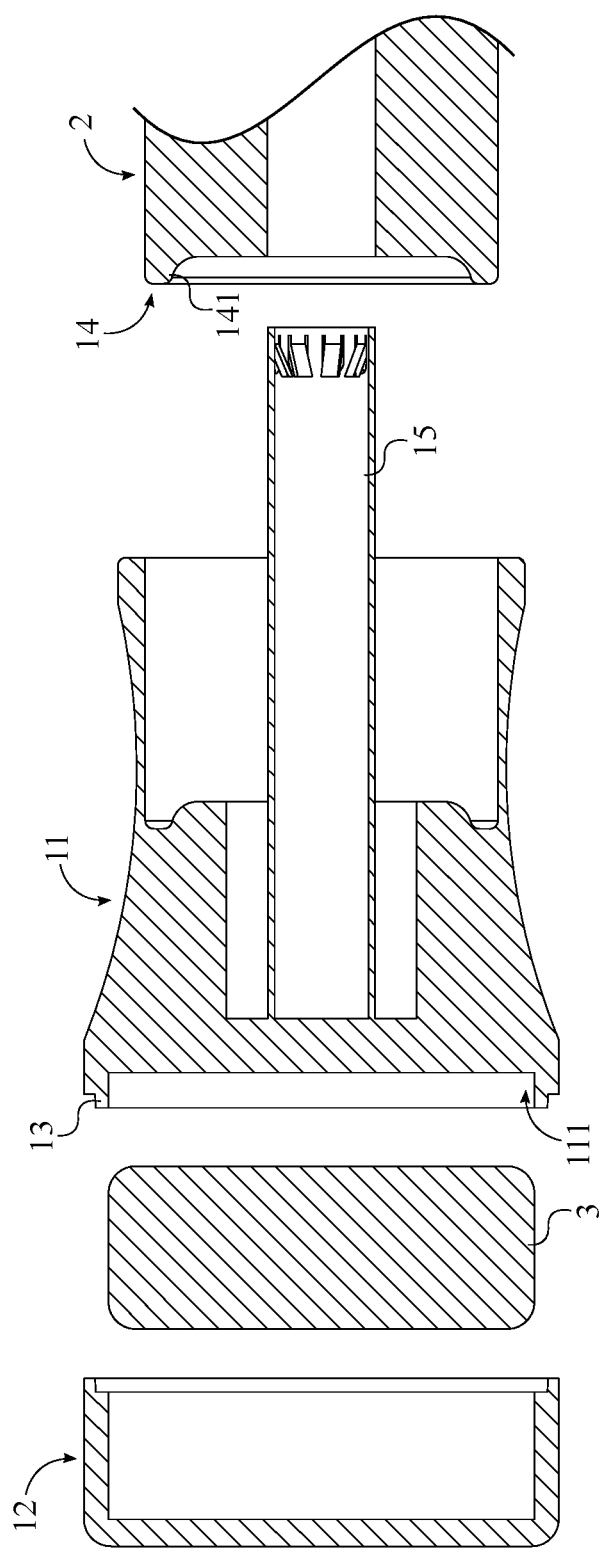
FIG. 4 is a cross sectional view taken along line 4-4 in FIG. 3 illustrating the cover fastener and the coupling interface.

Referring to FIG. 3 and FIG. 4, preferably, the antiseptic-soaked dressing 3 is impregnated with an antiseptic-antibacterial solution that disinfects and sanitizes the patient's skin. As the name implies, the antiseptic-soaked dressing 3 is made of absorbent foam or cloth that absorbs and retains the antibacterial-antiseptic solution until the administration of the injection. Unlike conventional autoinjectors which require a separate medical kit for holding the antiseptic-soaked dressing 3, the present invention uses the cap assembly 1 to house the antiseptic-soaked dressing 3. As such, the cap assembly 1 comprises a receptacle 11, a removable cover 12, a cover fastener 13, and a coupling interface 14. The receptacle 11 is preferably a hollow cylindrical structure that houses the antiseptic-soaked dressing 3. The removable cover 12 is similarly a hollow cylindrical structure that seals the antiseptic-soaked dressing 3 within the receptacle 11, thereby preventing the antiseptic-soaked dressing 3 from drying out. The cover fastener 13 fastens the removable cover 12 to the receptacle 11. Similarly, the coupling interface 14 couples the receptacle 11 to the autoinjector body 2, thereby coupling the cap assembly 1 to the autoinjector body 2 as well. The antiseptic-soaked dressing 3 is mounted within the cap assembly 1. Placing the antiseptic-soaked dressing 3 in the cap assembly 1 for pre-injection treatment obviates the need to carry pre-injection treatment materials in a separate container.

Referring more specifically to FIG. 4, the removable cover 12 is attached across an opening 111 of the receptacle 11 by the cover fastener 13. Similarly, the coupling interface 14 is connected adjacent to the receptacle 11, opposite the removable cover 12. More specifically, the autoinjector body 2 and the removable cover 12 attach at opposite ends of the cap assembly 1. As such, the antiseptic-soaked dressing 3 is positioned between the receptacle 11 and the removable cover 12. To connect the cap assembly 1 to the autoinjector body 2, the coupling interface 14 is engaged to the autoinjector body 2. A pull tab that is preferably mounted to the rim of the removable cover 12 allows the removable cover 12 to easily disengage the receptacle 11, thereby exposing the antiseptic-soaked dressing 3. The administrator may then rub the antiseptic-soaked dressing 3 against the patient's skin, thereby treating the injection area. Once the injection area is treated, the administrator may remove the receptacle 11 and deliver the injection.

In the preferred embodiment of the present invention, the coupling interface 14 is a slip-fit fastener 141 that selectively fastens the cap assembly 1 to the autoinjector. The slip-fit fastener 141 can establish a secure connection between the receptacle 11 and a variety of different autoinjectors currently in the market. Alternately, the coupling interface 14 may utilize snaps, screws, magnets, or any number of fastening mechanisms capable of securely connecting with the autoinjector body 2. The slip-fit fastener 141 is a cylindrical extrusion fabricated to fine tolerances. The slip-fit fastener 141 slides into a cylindrical slot made into the autoinjector body 2 that is dimensioned slightly thicker than the slip-fit fastener 141. The cylindrical slot is positioned adjacent to the needle-end of the autoinjector body 2, thereby allowing the cap assembly 1 to cover the needle until the time of the delivery. In an alternate embodiment of the present invention, the cylindrical slot may be positioned opposite the needle-end of the autoinjector body 2. In yet another embodiment of the present invention, the cap assembly 1 may be modified to attach to a terminating end of a syringe plunger or a needle-end of the syringe.

Referring more specifically to FIG. 2 and FIG. 4, in the preferred embodiment of the present invention, the antiseptic-soaked dressing 3 is connected into the receptacle 11. As a result, the administrator can apply the antiseptic-soaked dressing 3 to the injection area without removing the receptacle 11 from the autoinjector body 2. In addition, the administrator can leverage the autoinjector body 2 to more accurately apply the antiseptic-soaked dressing 3 to the desired injection area. Preferably, the antiseptic-soaked dressing 3 is attached or fastened into the opening 111 of the receptacle 11. More specifically, the antiseptic-soaked dressing 3 may be attached or coupled to the opening 111 of the receptacle 11 via a friction fit, snap fit adhesive, fastener, or another suitable means that is within the spirit and scope of the present invention. As the antiseptic-soaked dressing 3 is longer than the depth of the cavity, the antiseptic-soaked dressing 3 traverses out of the opening 111 of the receptacle 11. As such, the removable cover 12 is used to enclose the exposed end of the antiseptic-soaked dressing 3.

Figure 5:
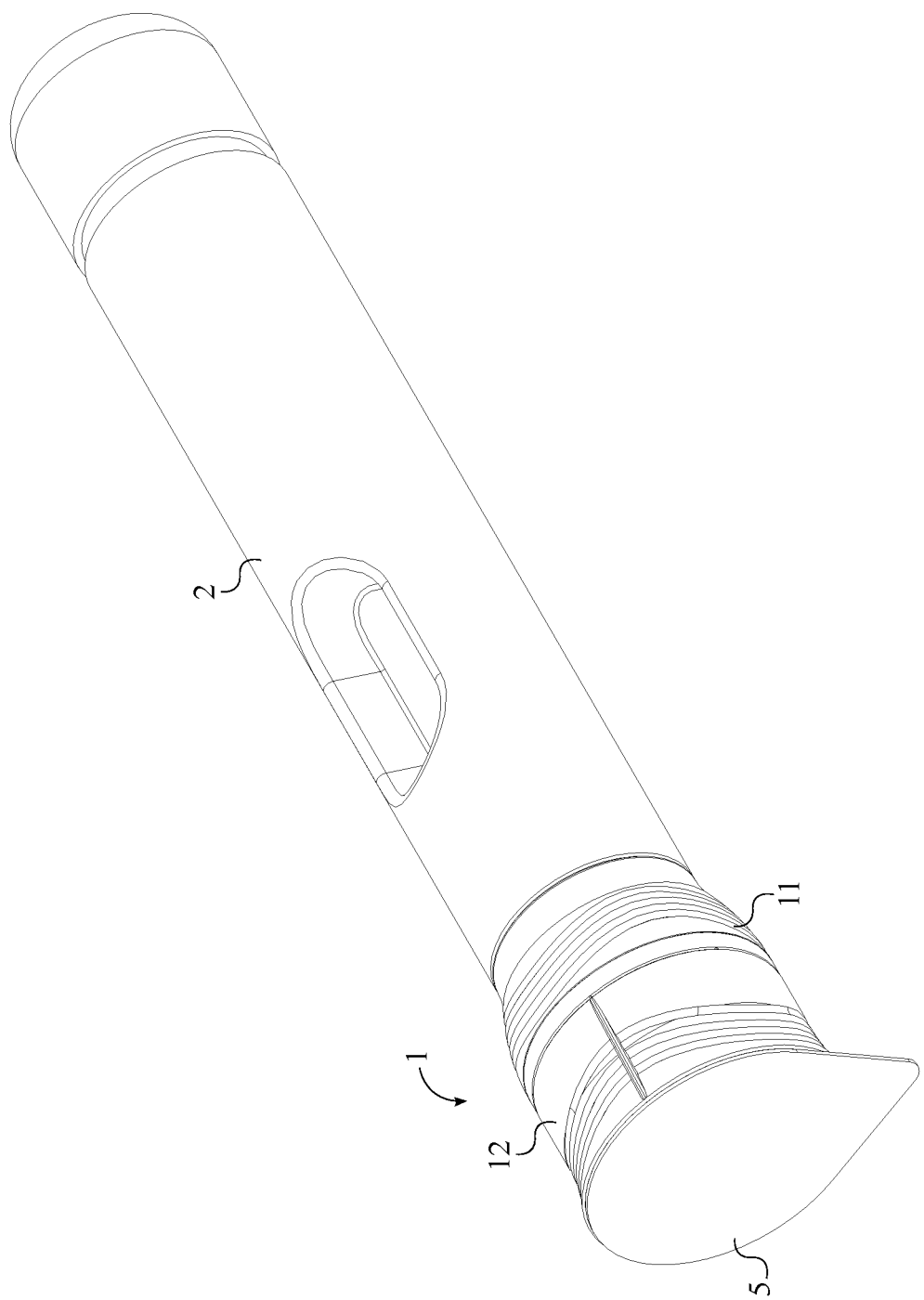
FIG. 5 is a front perspective view of an alternate embodiment, wherein the antiseptic-soaked dressing is attached to the removable cover.
Figure 6:
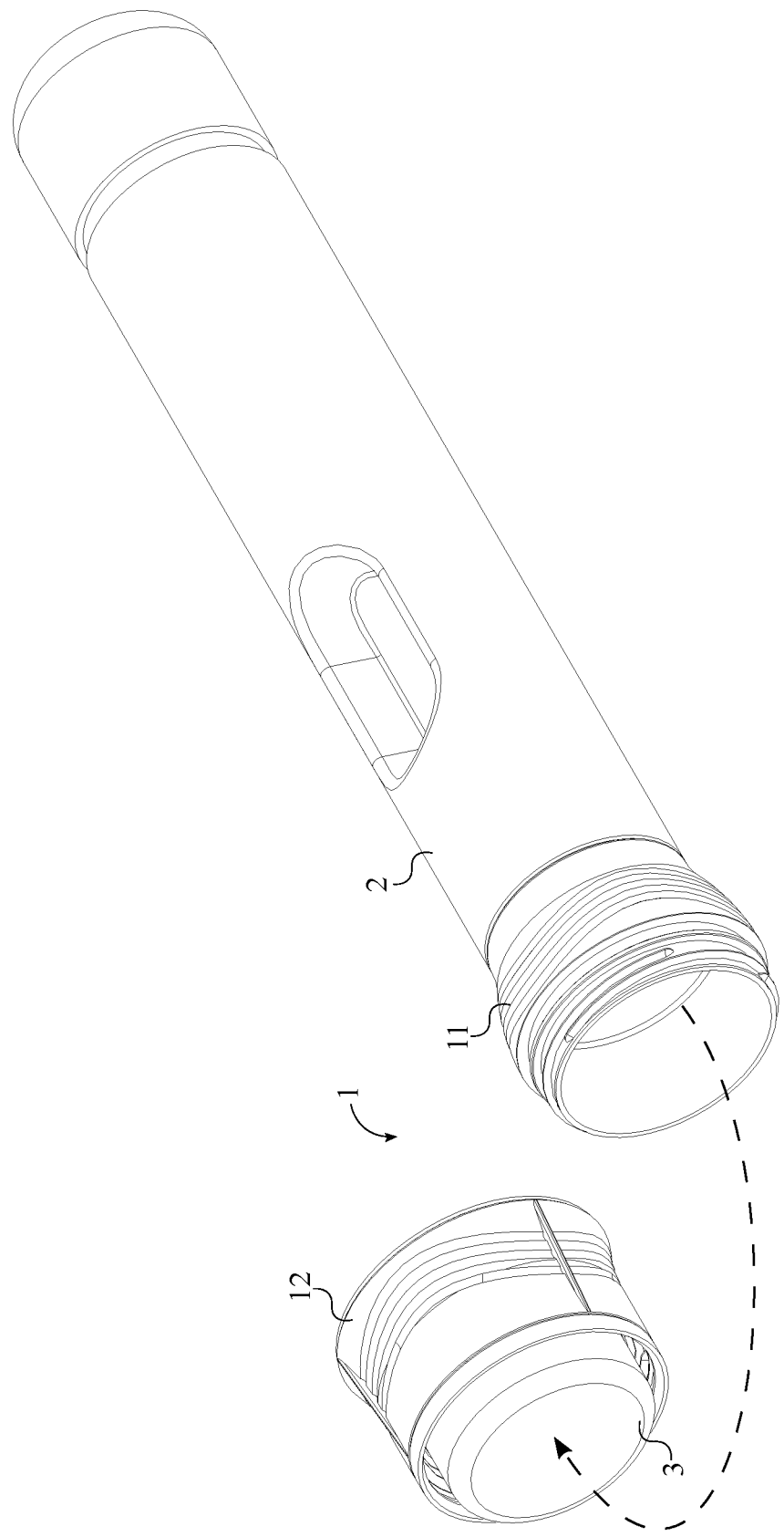
FIG. 6 is a front perspective view of alternate embodiment with the removable cover detached from the receptacle.

Referring to FIG. 5 and FIG. 6, in an alternate embodiment of the present invention, the antiseptic-soaked dressing 3 is connected to the removable cover 12. More specifically, the antiseptic-soaked dressing 3 is attached or fastened onto an opening of the removable cover 12. The antiseptic-soaked dressing 3 traverses into the opening 111 of the receptacle 11. Thus, similarly allowing the antiseptic-soaked dressing 3 to be positioned in between the receptacle 11 and the removable cover 12. In this embodiment, the administrator must separate the antiseptic-soaked dressing 3 from the autoinjector body 2 to treat the injection area. This prevents accidentally activating the injection mechanism of the autoinjector while treating the injection area.

Figure 7:
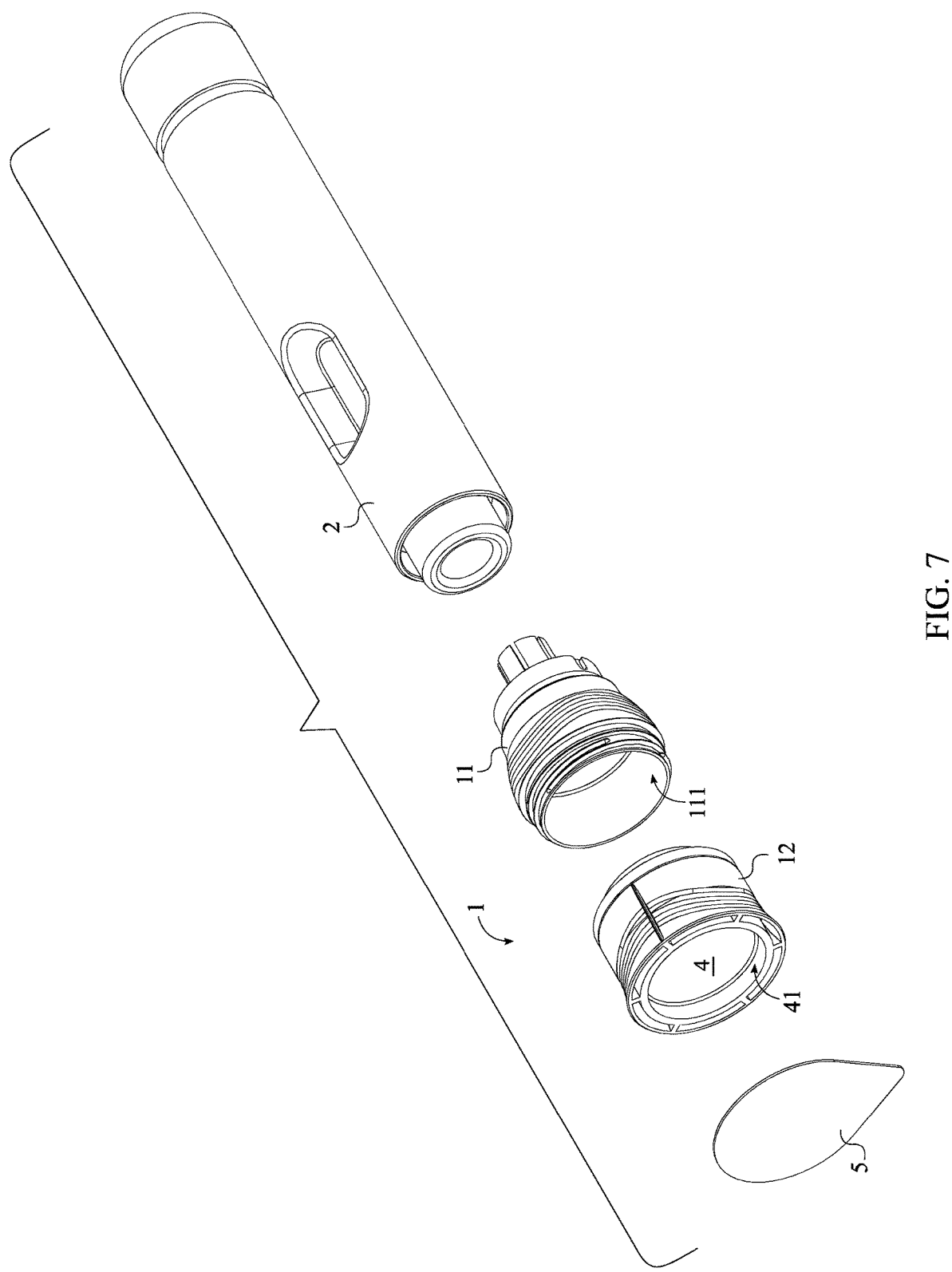
FIG. 7 is an exploded view of the alternate embodiment showing the cover lid detached from the storage compartment.

Referring to FIG. 7, as mentioned previously, the present invention is also a system for facilitating the post-injection treatment process. As such, a storage compartment 4 is provided to house post-injection treatment materials. The storage compartment 4 is secured with a cover lid 5. Preferably, the storage compartment 4 is integrated into the removable cover 12, opposite to the receptacle 11. Further, the cover lid 5 is attached across an opening 41 of the storage compartment 4. The opening 41 preferably faces away from the autoinjector body 2 in the engaged position. As such, the storage compartment 4 can be accessed without having to disengage the removable cover 12 from the receptacle 11. Post-injection treatment materials may refer to a gauze and a bandage for covering the injection area. The cover lid 5 is designed to securely enclose the storage compartment 4 until it is time to deliver the injection. Preferably, the cover lid 5 is a die-cut sheet of aluminum that is heat sealed onto the removable cover 12. Alternately, the cover lid 5 can be any type of plastic or paper closure. As such, the cover lid 5 is reinforced against forward and side impacts, as those that occur from being dropped on the floor or knocked against hard objects. However, the heat seal is weak enough to allow the administrator to easily peel the cover lid 5 off the removable cover 12 to access the gauze and the bandage. Once the injection is successfully delivered, the administrator uses the gauze and bandages in the storage compartment 4 to dress the injection area. More specifically, the administrator may position the gauze over the injection area such that the gauze absorbs blood escaping from the hole left by the needle of the autoinjector body 2. Next, the administrator may attach the bandage over the gauze to secure the gauze to the patient's body.

Figure 8:
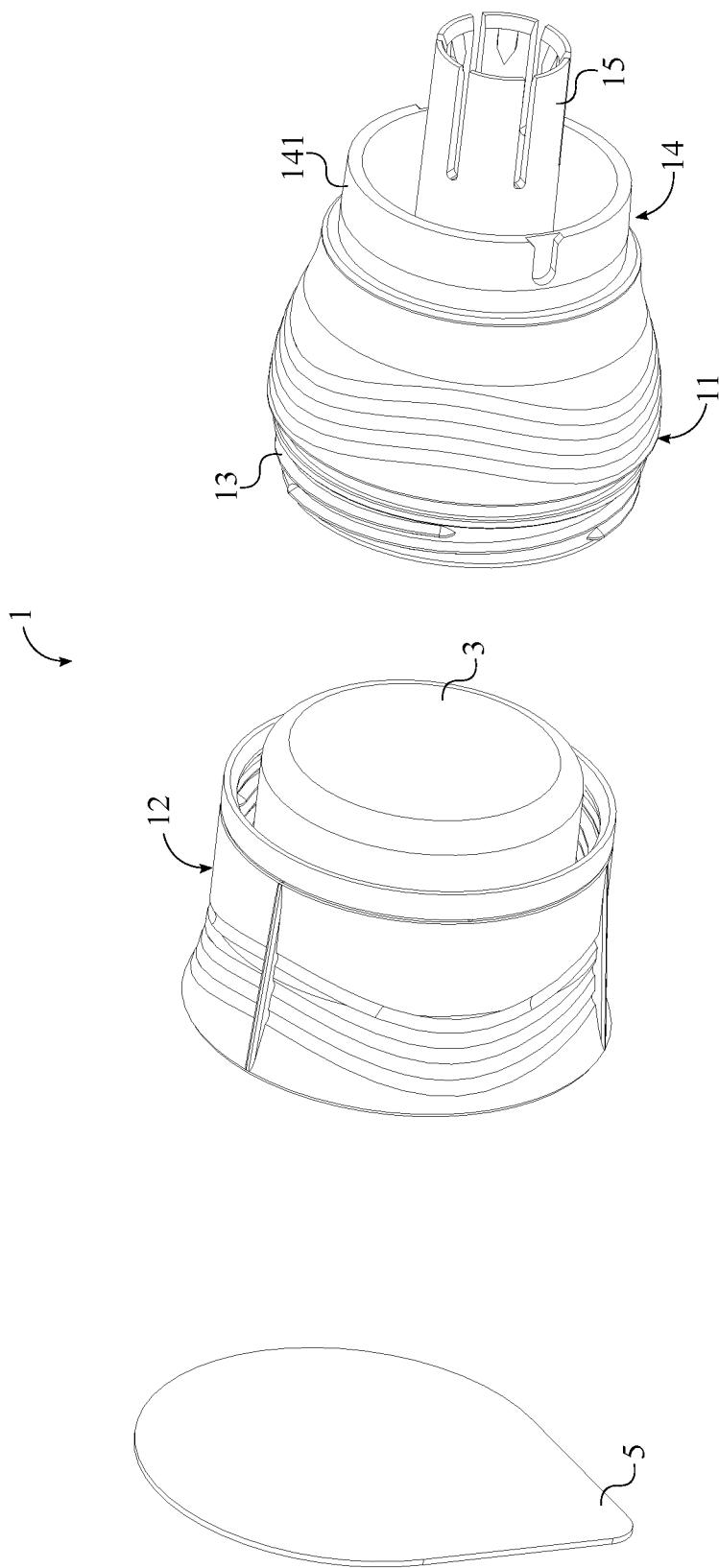
FIG. 8 is a rear perspective exploded view of alternate embodiment illustrating the cover fastener.

Referring to FIG. 8, when the antiseptic-soaked dressing 3 is connected to the removable cover 12, the removable cover 12 is threadably engaged to the receptacle 11. More specifically, the cover fastener 13 comprises external threads and internal threads. The external threads are terminally connected to the receptacle 11, whereas the internal threads are terminally connected to the removable cover 12. Accordingly, the removable cover 12 can be screwed onto the receptacle 11. Alternately, when the antiseptic-soaked dressing 3 is mounted onto the receptacle 11, the cover fastener 13 may be snap fasteners, slip-fit slots, and/or magnetic fasteners.

A needle shield fitted over the needle of the autoinjector body 2 prevents the needle from being contaminated and/or damaged prior to the delivery of the injection. To remove the needle shield, the cap assembly 1 further comprises a needle-shield remover 15. As such, the needle-shield remover 15 is connected to the receptacle 11. More specifically, the needle-shield remover 15 is a slender tube that fits over the needle shield. Further, the needle-shield remover 15 is positioned amongst the coupling interface 14, wherein the needle-shield remover 15 covers a needle of the autoinjector housing when the cap assembly 1 is mounted to the autoinjector body 2. As such, when the cap assembly 1 is pulled off the autoinjector body 2, the needle-shield remover 15 pulls the needle shield off the needle.

Figure 9:
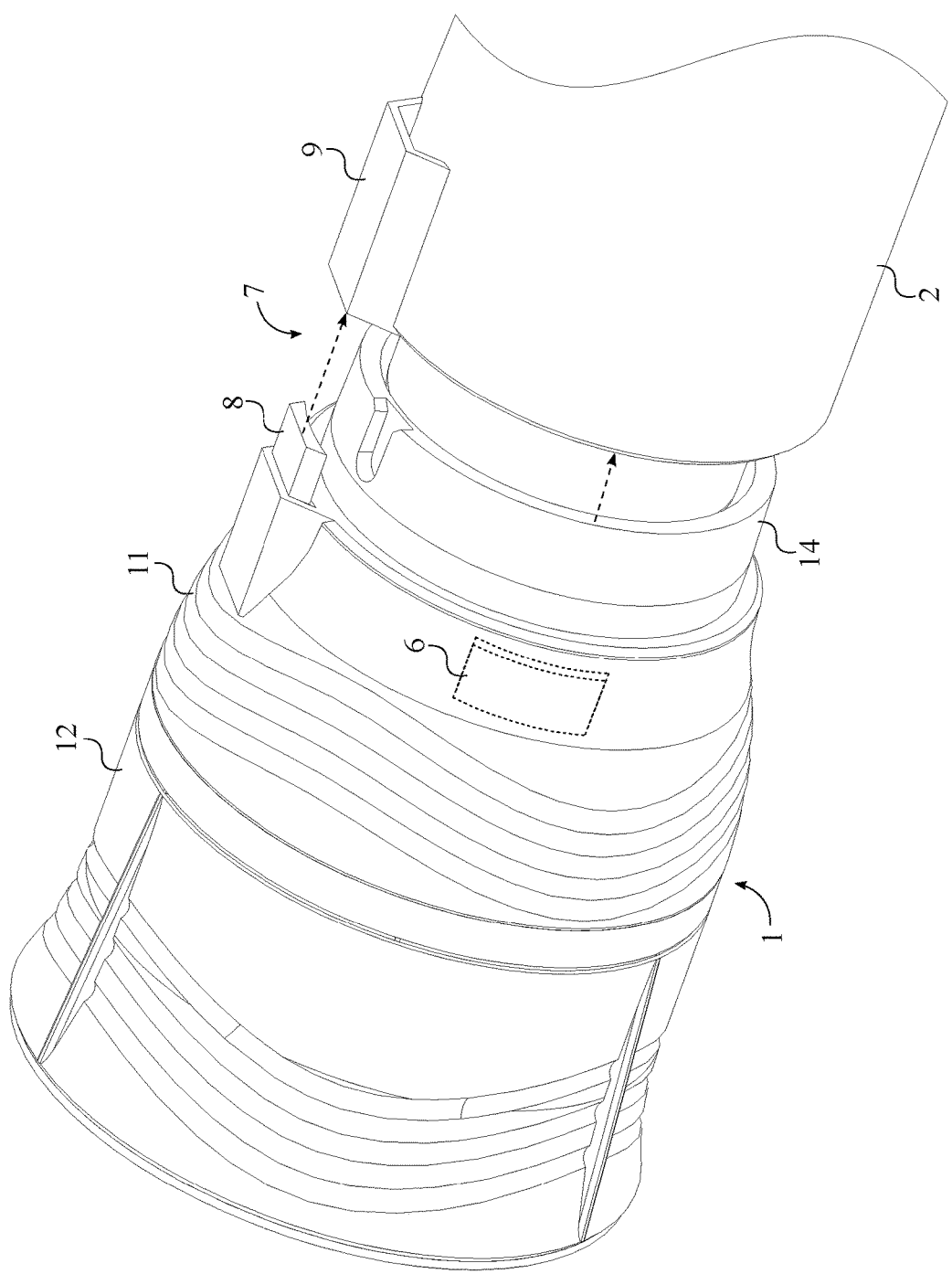
FIG. 9 is rear perspective view of the present invention illustrating the operation of the locking mechanism.

Referring to FIG. 9, preferably, the autoinjector body 2 is used to inject liquid or gas solutions with limited shelf-life that are ineffective past the expiration date. Thus, the present invention comprises an expiration timer 6, which keeps track of the expiration date, and a locking mechanism 7, which prevents the delivery of expired solutions. The expiration timer 6 is mounted within the cap assembly 1 and can engage the locking mechanism 7 once the expiration date has passed. Moreover, the locking mechanism 7 is operatively integrated into the cap assembly 1, wherein the locking mechanism 7 is used to selectively secure the cap assembly 1 to the autoinjector body 2. As such, the locking mechanism 7 creates a permanent lock between the cap assembly 1 and the autoinjector body 2, thereby sealing the needle in the autoinjector body 2. Similarly, the expiration timer 6 is operatively coupled to the locking mechanism 7, wherein the expiration timer 6 is used to actuate the locking mechanism 7. Preferably, the expiration timer 6 is a microcontroller programmed to keep track of the expiration date. In one possible embodiment, the expiration timer 6 may be programmed during the fabrication of the cap assembly 1. Alternately, a user interface may be provided to allow the administrator to program the expiration timer 6.

Since the cap assembly 1 is designed to be retrofitted onto existing autoinjectors, it is desirable to integrate both the expiration timer 6 and the locking mechanism 7 into the cap assembly 1. Accordingly, the locking mechanism 7 is integrated into the removable cover 12. More specifically, the locking mechanism 7 comprises a male connector 8 and the female connector 9. The female connector 9 is laterally mounted onto the autoinjector body 2. The male connector 8 is slidably mounted onto the removable cover 12. The longitudinal axis of the male connector 8 is coincident to the longitudinal axis of the female connector 9. In the preferred embodiment of the present invention, the male connector 8 and the female connector 9 may operate similarly to a snap-fit buckle. The male connector 8 may comprise cantilever member, and the female connector 9 may comprise a slot. Once the expiration date passes, the expiration timer 6 activates the locking mechanism 7 by sliding the cantilever member into the slot. This forms a snap-fit between the male connector 8 and the female connector 9, which permanently secures the cap assembly 1 to the autoinjector body 2.

Alternately, the locking mechanism 7 may comprise any number of fastening mechanisms well known in the arts. For example, the locking mechanism 7 may comprise screws, snaps, magnets, or any number of fasteners well known in the arts.

Although the invention has been explained in relation to its preferred embodiment, it is to be understood that many other possible modifications and variations can be made without departing from the spirit and scope of the invention as hereinafter claimed.

What is claimed is:

1. A system for integrating an antibacterial-element receptacle into a cap, wherein the system comprises:
    a cap assembly;
    a body;
    an antiseptic-soaked dressing;
    the cap assembly comprising a receptacle, a removable cover, a cover fastener, and a coupling interface;
    the removable cover being attached across an opening of the receptacle, by the cover fastener;
    the coupling interface being connected adjacent to the receptacle, opposite the removable cover;
    the coupling interface being engaged to the body;
    the antiseptic-soaked dressing being mounted in between the removable cover and the receptacle;
    the antiseptic-soaked dressing being connected onto the removable cover;
    the antiseptic-soaked dressing traversing into the opening of the receptacle;
    a storage compartment;
    a cover lid;
    the storage compartment being integrated into the removable cover, opposite to the receptacle; and
    the cover lid being attached across an opening of the storage compartment.

2. The system as claimed in claim 1, wherein the coupling interface is a slip-fit fastener.

3. The system as claimed in claim 1, wherein the system further comprises:
    the removable cover being threadably engaged to the receptacle.

4. The system as claimed in claim 1, wherein:
    the cap assembly further comprises a needle-shield remover; and
    the needle-shield remover is connected adjacent to the receptacle.

5. The system as claimed in claim 1, wherein the system further comprises:
    an expiration timer;
    a locking mechanism;
    the expiration timer being mounted within the cap assembly;
    the locking mechanism being operatively integrated into the cap assembly, wherein the locking mechanism is used to selectively secure the cap assembly to the body; and
    the expiration timer being operatively coupled to the locking mechanism, wherein the expiration timer is used to actuate the locking mechanism.

6. The system as claimed in claim 5, wherein:
    the locking mechanism comprises a male connector and a female connector;
    the female connector is laterally mounted onto the body;
    the male connector is slidably mounted onto the removable cover; and a longitudinal axis of the male connector is coincident to a longitudinal axis of the female connector.

7. A system for integrating an antibacterial-element receptacle into a cap comprises:
   a cap assembly;
   a body;
   an antiseptic-soaked dressing;
   an expiration timer;
   a locking mechanism;
   the cap assembly comprising a receptacle, a removable cover, a cover fastener, and a coupling interface;
   the removable cover being attached across an opening of the receptacle by the cover fastener;
   the coupling interface being connected adjacent to the receptacle, opposite the removable cover;
   the coupling interface being engaged to the body;
   the antiseptic-soaked dressing being mounted in between the removable cover and the receptacle;
   the expiration timer being mounted within the cap assembly;
   the locking mechanism being operatively integrated into the cap assembly; wherein the locking mechanism is used to selectively secure the cap assembly to the body; and
   the expiration timer being operatively coupled to the locking mechanism, wherein the expiration timer is used to actuate the locking mechanism.

8. The system as claimed in claim 7, wherein:
   the locking mechanism comprises a male connector and a female connector;
   the female connector is laterally mounted onto the body;
   the male connector is slidably mounted onto the removable cover; and
   a longitudinal axis of the male connector is coincident to a longitudinal axis of the female connector.

9. The system as claimed in claim 7, wherein the coupling interface is a slip-fit fastener.

10. The system claimed in claim 7, wherein the system further comprises:
    the antiseptic-soaked dressing being connected into the receptacle; and
    the antiseptic-soaked dressing traversing out of the opening of the receptacle.

11. The system as claimed in claim 7, wherein the system further comprises:
    the antiseptic-soaked dressing being connected onto the removable cover; and
    the antiseptic-soaked dressing traversing into the opening of the receptacle.

12. The system as claimed in claim 11, wherein the system further comprises:
    a storage compartment;
    a cover lid;
    the storage compartment being integrated into the removable cover, opposite to the receptacle; and
    the cover lid being attached across an opening of the storage compartment.

13. The system as claimed in claim 11, wherein the system further comprises:
    the removable cover being threadably engaged to the receptacle.

14. The system as claimed in claim 7, wherein:
    the cap assembly further comprises a needle-shield remover; and
    the needle-shield remover is connected adjacent to the receptacle.

* * * * *